US012806233B2

(12) United States Patent
Ruff

(10) Patent No.: US 12,806,233 B2
(45) Date of Patent: Nov. 24, 2026

(54) METHODS FOR TREATING SUBCLINICAL MASTITIS IN RUMINANTS

(71) Applicant: Stratum Nutrition, Carthage, MO (US)

(72) Inventor: Kevin James Ruff, Springfield, MO (US)

(73) Assignee: Stratum Nutrition, Carthage, MO (US)

( * ) Notice: Subject to any disclaimer, the term of this patent is extended or adjusted under 35 U.S.C. 154(b) by 382 days.

(21) Appl. No.: 18/371,609

(22) Filed: Sep. 22, 2023

(65) Prior Publication Data

US 2025/0099510 A1 Mar. 27, 2025

(51) Int. Cl.

| | |
|---|---|
| ***A61K 35/57*** | (2015.01) |
| ***A61K 9/00*** | (2006.01) |
| ***A61K 31/7004*** | (2006.01) |
| ***A61K 31/7008*** | (2006.01) |
| ***A61K 31/728*** | (2006.01) |
| ***A61K 38/01*** | (2006.01) |
| ***A61P 31/04*** | (2006.01) |

(52) U.S. Cl.

CPC ............ *A61K 35/57* (2013.01); *A61K 9/0053* (2013.01); *A61K 31/7004* (2013.01); *A61K 31/7008* (2013.01); *A61K 31/728* (2013.01); *A61K 38/014* (2013.01); *A61P 31/04* (2018.01)

(58) Field of Classification Search

CPC .. A61K 35/57; A61K 9/0053; A61K 31/7004; A61K 31/7008; A61K 31/728; A61K 38/014; A61K 9/148; A61P 31/04

See application file for complete search history.

(56) References Cited

U.S. PATENT DOCUMENTS

| | | | |
|---|---|---|---|
| 8,580,315 | B2 | 11/2013 | DeVore et al. |
| 10,328,104 | B2 | 6/2019 | Ruff |

FOREIGN PATENT DOCUMENTS

| | | | | | |
|---|---|---|---|---|---|
| JP | 3051268 | B2 * | 6/2000 | | |
| WO | WO-2025063956 | A1 * | 3/2025 | ........... | A61K 31/728 |

OTHER PUBLICATIONS

Esai Co, Ltd. (JP3051268B2) [Google Patents English Machine Translation] (Year: 2000).*

Yoo, et al., "Effects of Egg Shell Membrane Hydrolysates on Anti-Inflammatory, Anti-Wrinkle, Anti-Microbial Activity and Moisture-Protection." Korean J Food Sci Anim Resour. 2014;34(1):26-32. (Year: 2014).*

CD69 expression as an index of T-cell function: assay standardization, validation and use in monitoring immune recovery—WB Lindsey, et al.—Cytotherapy (2007)—vol. 9, No. 2, pp. 123-132.

The Leukocyte Activation Receptor CD69 Controls T Cell Differentiation through Its Interaction with Galectin-1—Hortensia de la Fuente, et al.—Molecular and Cellular Biology—Jul. 2014—vol. 34, No. 13, pp. 2479-2487.

* cited by examiner

*Primary Examiner* — Thomas J. Visone

(74) *Attorney, Agent, or Firm* — Hoffmann & Baron LLP

(57) ABSTRACT

The invention provides a method for treating subclinical mastitis in a ruminant by orally administering to the ruminant an effective amount of a composition that contains a naturally occurring material derived from eggshell membrane.

16 Claims, No Drawings

METHODS FOR TREATING SUBCLINICAL MASTITIS IN RUMINANTS

BACKGROUND

Mastitis in ruminants, particularly dairy cows, occurs when microbes enter the teat of a ruminant's udder via the teat canal. Almost any microbe can opportunistically invade the teat canal and cause mastitis. However, most infections are caused by various species of *streptococci* (or similar gram-positive cocci), *staphylococci*, and gram-negative rods, especially lactose-fermenting organisms of enteric origin, commonly called coliforms. Contagious transmission of infection from one cow to another primarily occurs during milking, through such pathways as milkers' hands or the liners of the milking unit. Other sources of transmission can be from contaminated teat dips, intramammary infusions, water used for udder preparation before milking, water ponds or mud holes, and skin lesions. Intramammary infections (IMIs) are often described as either clinical or subclinical mastitis. Clinical mastitis is an immune-mediated inflammatory response to infection causing visibly abnormal milk (e.g. color, fibrin clots, etc.). As the extent of the inflammation increases, changes in the udder (swelling, heat, pain, redness) may also be apparent. Conversely, subclinical mastitis is the presence of an infection without apparent signs of local inflammation or systemic involvement. Although transient episodes of abnormal milk may appear, subclinical mastitis is, for the most part, asymptomatic. Once established, many of these subclinical infections persist for entire lactations or the life of the cow, although this varies with the causative pathogen. All dairy herds have cows with subclinical mastitis, however prevalence of infected cows can vary from 5%-75%. Detection of subclinical mastitis is best done by testing milk for somatic cell counts (SCCs) (predominantly leukocytes). SCCs are positively correlated with the presence of infection. Increased levels of SCCs impact the shelf life and flavor of milk. A lower SCC is better for cheese production and gives a longer shelf life for bottled milk. Because of this, milk processors pay a premium for milk with low SCCs. Milk yield also decreases in cows with subclinical mastitis. The loss of milk from subclinical mastitis is directly proportional to the individual cow's SCC. As SCC rises, milk production decreases. These losses can be especially significant if an IMI occurs in early lactation and persists as a chronic infection throughout lactation.

Antibiotics are the primary treatment for clinical mastitis, however any treated cows must be taken out of the milking pool for a period of time to prevent contamination of the milk supply with antibiotic residues. Dry cow therapy is more economical and much less likely to result in therapeutic residues in milk compared with lactating cow therapy, however this also results in decreased milk production for a farm. Therapy for subclinical mastitis is generally only given on the premise that treatment costs will be outweighed by milk production gains after elimination of the infection, however prevention of subclinical mastitis is preferred.

Immune function of leukocytes in a lactating gland is impaired compared with other tissues of the body, therefore subclinical mastitis is poorly cleared by ruminant's own immune system. Consequently, methods of enhancing immune cell function in mammary tissues are of great interest to dairy farmers and could be a possible treatment for subclinical mastitis. Eggshell membrane (ESM) isolated from chicken (*Gallus gallus*) eggshells has been shown to have antibacterial properties and the ability to activate immune cells. Thus, the present invention describes methods of treating subclinical mastitis in ruminants via oral administration of a naturally occurring material derived from eggshell, eggshell membrane, or a combination thereof.

SUMMARY OF THE INVENTION

These objectives, among others, are addressed by the present invention.

A first embodiment of the invention is a method for treating subclinical mastitis in a ruminant in need by orally administering to the ruminant an effective amount of a composition comprising a naturally occurring material derived from eggshell membrane.

In one embodiment, the effective amount of composition comprising a naturally occurring material derived from eggshell membrane is effective to achieve at least about a 0.5 percentage point decrease in somatic cell count.

In another embodiment, the effective amount of composition comprising a naturally occurring material derived from eggshell membrane is effective to achieve at least about a 1 percentage point decrease in somatic cell count.

In yet another embodiment, the effective amount of composition comprising a naturally occurring material derived from eggshell membrane is effective to achieve at least about a 2 percentage point decrease in somatic cell count.

Alternatively, the effective amount of composition comprising a naturally occurring material derived from eggshell membrane is effective to achieve at least about a 5 percentage point decrease in somatic cell count.

In some embodiments, the naturally occurring material is selected from a hexosamine, a glycosaminoglycan, hyaluronic acid, sialic acid, a collagen, elastin, other egg proteins or glycoproteins, lysozyme, ovotransferrin, lysyl oxidase, and/or a combination thereof.

Preferably, the hexosamine is glucosamine and/or N-acetylglucosamine.

More preferably, the glycosaminoglycan is chondroitin sulfate, dermatan sulfate, keratan sulfate, heparan sulfate, and/or a combination thereof.

In one embodiment, the naturally occurring material is water soluble. In another, the naturally occurring material is water insoluble.

According to the invention, the naturally occurring material comprises the following in weight percent:

about 0.1 to about 5 wt % hexosamine;

about 0.1 to about 3 wt % glycosaminoglycan;

about 0.5 to about 5 wt % hyaluronic acid;

about 0.01 to about 2 wt % sialic acid; and/or about 3 to about 20 wt % collagen.

In some embodiments of the invention, the naturally occurring material is an eggshell membrane powder. In other embodiments, the naturally occurring material is an eggshell membrane extract.

In other embodiments, the naturally occurring material is an eggshell membrane hydrolysate or an eggshell membrane isolate.

In a preferred embodiment, the eggshell membrane is a fowl eggshell membrane.

DETAILED DESCRIPTION

In one aspect, the invention relates to a method for treating subclinical mastitis. The method includes orally administering to a ruminant in need thereof an effective amount of a composition. The composition includes a naturally occurring material derived from eggshell membrane.

For the purposes of the present invention, subclinical mastitis is defined as having a somatic cell count (SCC) of about 100,000 cells/milliliter (mL) or more. More preferably, a SCC of about 10,000 cells/mL or more. Still more preferably, a SCC of about 1,000 cells/mL or more. Most preferably, a SCC of about 100 cells/mL or more.

The present invention is suitable for veterinary uses. Suitable subjects include, but are not limited to, ruminant subjects; preferably, cows, goats, sheep, and camels. For example, the ruminant can be a female of lactating age.

A ruminant in need of the methods of the invention includes (i) ruminants suffering from subclinical mastitis; (ii) ruminants at risk for or prone to developing subclinical mastitis; and (iii) any ruminant in which subclinical mastitis is to be prevented.

Administration

The methods of the invention include administering to a ruminant in need thereof an effective amount of the composition. For oral administration, the composition may be in the form of any unit dosage vehicle, such as a capsule or tablet, or in the form of powder, liquid, or contained in any convenient food item. The composition may also include pharmaceutically or nutraceutically active ingredients, fillers, binders, lubricants, flow agents, colorants, or other processing agents.

In one embodiment, the effective amount of the composition administered in accordance with the method of the invention is any amount effective for treating subclinical mastitis. In another embodiment, the effective amount of the composition administered in accordance with the method of the invention is any amount effective for reducing incidence subclinical mastitis. In yet another embodiment, the effective amount of the composition administered in accordance with the method of the invention is any amount effective for preventing subclinical mastitis.

The administered amount of the composition will vary according to numerous factors that are well known in the art, such as the route of administration, the particular ruminant to be treated, the status of the subclinical mastitis in the subject, the body weight of the subject, etc. The appropriate amount of the composition can readily be determined by those skilled in the art.

For example, the effective amount of the composition may be any amount that is sufficient to achieve a decrease in somatic cell count. In one embodiment, the effective amount is effective to achieve at least about a 0.5 percentage point, at least about a 1 percentage point, at least about a 5 percentage point, at least about a 10 percentage point, or at least about a 20 percentage point decrease in SCC in the subject. Methods of determining percentage point decrease of SCC in a ruminant are known in the art.

A ruminant in need of a method of the invention may have a somatic cell count (SCC) that is greater than about 10 cells/mL, about 20 cells/mL, about 50 cells/mL, about 100 cells/mL, about 1,000 cells/mL, about 5,000 cells/mL, about 10,000 cells/mL, about 25,000 cells/mL, or about 100,000 cells/mL or greater.

The methods of the present invention may be combined with any known treatment or prevention regimen for clinical or subclinical mastitis. The methods and compositions of the invention may be simultaneously, separately or sequentially administered with any known treatment regimens.

In a preferred embodiment, a composition of the present invention may be administered long-term for the methods of the invention. In this regard, the composition may be administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The compositions may also be administered for an administration period of at least 1, 2, 3, 4, 5, 6, 7, 8, 9, 10, 11, 12 or more months. The compositions may also be administered for an administration period of at least 1, 2, 3, 4, 5, 6, 78, 9, 10 or more years. During the administration period, the composition may be administered once daily, twice daily, thrice daily, or periodically, such as every other day, etc.

The composition of the present invention may also be administered intermittently for the methods of the invention. For example, the composition may be administered for an administration period of 1, 2, 3, 4, 5, or more weeks, followed by a period of discontinuance, followed by an administration period of 1, 2, 3, 4, 5 or more weeks.

Composition

The composition used in the methods of the invention includes a naturally occurring material. The terms, "natural material," "naturally occurring material" or "naturally occurring active material" derived from eggshell, eggshell membrane, or a combination thereof refer to material that contains a significant amount of at least one ingredient or component of the eggshell, eggshell membrane, or a combination thereof that is substantially unaltered from an untreated or unprocessed eggshell, eggshell membrane, or a combination thereof, respectively. "Substantially unaltered" refers to a characteristic of a selected or desired ingredient(s) or component(s), having substantially retained its/their physical and/or chemical characteristics and is/are not significantly decomposed, digested or cleaved. However, other components or ingredients may be altered in certain isolates or hydrolysates. For example, hydrolysates prepared by enzyme treatment may result in naturally occurring proteins being at least partially digested.

Preferably, the majority of the naturally occurring ingredients found in the eggshell, eggshell membrane, or a combination thereof are substantially unaltered and, more preferably, substantially all of the naturally occurring ingredients are substantially unaltered. Although the physical characteristics of individual components of the eggshell, eggshell membrane, or a combination thereof remain substantially unaltered, the overall composition or amounts of different components can be altered depending on the desired composition for a particular isolate, extract or hydrolysate.

In one embodiment, the composition may contain a material derived from eggshell, eggshell membrane, or a combination thereof that is processed to be rich in water-soluble fractions of the respective eggshell, eggshell membrane, or a combination thereof that is rich in hyaluronic acid.

In another embodiment, the composition may contain a material derived from eggshell, eggshell membrane, or a combination thereof that is rich in water-insoluble fractions and/or is rich in certain collagens.

The material may also contain a specific component selected from the group consisting of a hexosamine, chondroitin sulfate, hyaluronic acid, collagen, other proteins, and combinations thereof. In one embodiment, the material includes at least about 10 wt % and at most about 80 wt % of other egg proteins or glycoproteins derived from eggshell, eggshell membrane, or a combination thereof, based on total weight of the material. It is also contemplated that the material derived from the eggshell, eggshell membrane, or a combination thereof can be processed to be rich in specific type(s) of collagen and/or proteins, depending upon the intended use.

In an embodiment of the invention, the material contains at least about 0.1 wt %, 0.25 wt %, 0.5 wt %, 1 wt %, 2 wt %, 3 wt %, 4 wt %, or about 4.5 wt % hexosamine, and the material contains at most about 10 wt %, 9 wt %, 8 wt %, 7 wt %, 6 wt %, or about 5 wt % hexosamine, based on the total weight of the material. Any minimum value may be combined with a maximum value in order to describe a range. Preferably, the material includes at least about 0.1 wt % and at most about 5 wt % hexosamine.

Examples of hexosamine include glucosamine, N-acetyl-D-glucosamine, glucosamine hydrochloride, glucosamine sulfate, and combinations thereof. Preferably, the hexosamine is glucosamine or N-acetyl-D-glucosamine.

In another embodiment, the material contains at least about 0.1 wt %, 0.2 wt %, 0.3 wt %, 0.4 wt %, 0.5 wt %, 0.6 wt %, 0.7 wt %, 0.8 wt %, 0.9 wt %, or about 1 wt % glycosaminoglycan, and the material contains at most about 5 wt %, 4 wt %, 3 wt %, 2.5 wt %, 2.0 wt %, or about 1.5 wt % glycosaminoglycans, based on the total weight of the material. Any minimum value may be combined with a maximum value in order to describe a range. Preferably, the material includes at least about 0.3 wt % and at most about 4% glycosaminoglycans.

Examples of glycosaminoglycans include chondroitin sulfate, dermatan sulfate, keratan sulfate, heparan sulfate, and combinations thereof.

In yet another embodiment, the material contains at least about 0.1 wt %, 0.2 wt %, 0.3 wt %, 0.4 wt %, 0.5 wt %, 1 wt %, 1.5 wt %, 2.0 wt %, 2.5 wt %, 3.0 wt %, 3.5 wt %, 4 wt % or about 4.5 wt % hyaluronic acid, and the material contains at most about 10 wt %, 9 wt %, 8 wt %, 7 wt %, 6 wt %, or about 5 wt % hyaluronic acid, based on the total weight of the material. Any minimum value may be combined with a maximum value in order to describe a range. Preferably, the material includes at least about 0.5 wt % and at most about 5% hyaluronic acid.

In a further embodiment, the material contains at least about 0.01 wt %, 0.02 wt %, 0.03 wt %, 0.04 wt %, 0.05 wt %, 0.06 wt %, 0.07 wt %, 0.08 wt %, 0.09 wt %, or about 0.1 wt % sialic acid, and the material contains at most about 3 wt %, 2.5 wt %, 2.0 wt %, 1.5 wt %, 1.0 wt % or about 0.5 wt % sialic acid, based on the total weight of the material. Any minimum value may be combined with a maximum value in order to describe a range. Preferably, the material includes at least about 0.01 wt % and at most about 2 wt % sialic acid.

In yet a further embodiment, the material contains at least about 1 wt %, 2 wt %, 3 wt %, 4 wt %, or 5 wt % collagen, and the material contains at most about 40 wt %, 35 wt %, 30 wt %, 25 wt %, 20 wt %, 15 wt %, or about 10 wt % collagen, based on the total weight of the material. Any minimum value may be combined with a maximum value in order to describe a range. Preferably, the material includes at least about 3 wt % and at most about 20 wt % collagen. The collagen can be a type selected from the group consisting of Type I collagen, Type III collagen, Type IV collagen, Type V collagen, Type VII collagen, Type VIII collagen, Type X collagen, Type XII collagen, Type XXII collagen and combinations thereof. All of these collagens have been found to be present in eggshell membrane.

The naturally occurring material may be derived from eggshell, eggshell membrane, or a combination thereof.

Known means to impart extended release to the eggshell membrane compositions are embodied by the present invention.

Eggshell

In one embodiment of the invention, the method includes orally administering to a mammal in need thereof an effective amount of a composition, which includes a naturally occurring material derived from eggshells, preferably fowl eggshells. Eggshell refers to the calcareous portion of eggs from which the eggshell membrane is removed. Suitable eggshells may be obtained from chickens or other birds and fowl, such as, for example, ducks, emu, ostrich, dove, quail, grouse, goose, turkey, ostrich, game hen, squab, pheasant, etc.

In one embodiment, the naturally occurring material derived from eggshell is an eggshell powder. For example, the eggshell material may be pulverized to produce an eggshell powder having a particle size between 100-500 microns. Powdering or pulverizing methods are known in the art.

In another embodiment, the naturally occurring material derived from eggshell is an eggshell extract. In yet another embodiment, the naturally occurring material derived from eggshell is an eggshell hydrolysate. In a further embodiment, the naturally occurring material derived from eggshell is an eggshell isolate.

Eggshell, processed eggshell, and eggshell hydrolysates or isolates contain naturally occurring materials derived from eggshell. These materials can be selected from the group consisting of a hyaluronic acid, hexosamine, chondroitin sulfate, collagen and combinations thereof.

The eggshell, processed eggshell, and eggshell hydrolysates and isolates are preferably free of any animal body components or traces thereof, e.g., animal tissue, blood or body fluid components, which are detrimental or undesirable for the contemplated use of the naturally occurring material or composition.

Although certain embodiments or examples may be described herein with reference to eggshell membrane, one skilled in the art can ascertain use of fowl eggshells. For example, one skilled in the art can ascertain various methods for processing of eggshells to obtain, extract, and/or purify the naturally occurring materials (i.e., hyaluronic acid, glucosamine, chondroitin sulfate, collagens) from eggshell sources. Such equivalents are intended to be encompassed in the scope of the present invention.

Eggshell Membrane

In one embodiment of the invention, the method includes orally administering to a mammal in need thereof an effective amount of a composition, which includes a naturally occurring material derived from eggshell membrane. Eggshell membrane is composed of two individual membranes between egg albumin and eggshell. The membranes are primarily comprised of protein fibers. The fibers appear to be a network or scaffold predominantly containing Type I collagen fibers that are encapsulated in a continuous mantle of proteoglycans and other macromolecules. The thickness of the two membranes ranges from 73-114 μm in eggs from White Leghorn and New England pullets. The outer membrane has a thickness ranging from 53.2 μm to 65.5 μm in White Leghorn eggs while the inner membrane ranges from 19.5 μm to 24.3 μm.

The proteins of shell membranes typically exhibit a high content of arginine, glutamic acid, methionine, histidine, cystine, and proline. Eggshell membranes also typically contain hydroxyproline, hydroxylysine, and desmosine. Type I, Type V, and Type X collagen are also typical in eggshell membrane.

Eggshell membrane also has been shown to contain acid glycosaminoglycans including dermatan sulfate and chondroitin-4-sulfate. Sulfated glycoproteins have been isolated from eggshell membrane. Glycoproteins in eggshell membrane include, for example, hexosamines, hexoses, and fucose.

In addition, hyaluronic acid has been detected in eggshell membrane. Other components identified in eggshell membrane include ovotransferrin, desmosine and isodesmosine, lysyl oxidase, and lysozyme.

In one embodiment, the naturally occurring material derived from eggshell membrane is an eggshell membrane powder. For example, the eggshell membrane material may be dehydrated to produce eggshell membrane flakes, which are then pulverized to produce an eggshell membrane powder having a particle size between 100-500 microns. Powdering or pulverizing methods are known in the art, such as, for example, by use of standard milling or pulverizing procedures to treat eggshell membrane flakes containing about 10% moisture.

In another embodiment, the naturally occurring material derived from eggshell membrane is an eggshell membrane extract. In yet another embodiment, the naturally occurring material derived from eggshell membrane is an eggshell membrane hydrolysate. In a further embodiment, the naturally occurring material derived from eggshell membrane is an eggshell membrane isolate.

Eggshell membrane, processed eggshell membrane, and eggshell membrane hydrolysates or isolates contain naturally occurring materials derived from eggshell membrane. These materials can be selected from the group consisting of hyaluronic acid, a hexosamine, chondroitin sulfate, a collagen and combinations thereof.

The eggshell membrane, processed eggshell membrane, and eggshell membrane hydrolysates and isolates are preferably free of any animal body components or traces thereof, e.g., animal tissue, blood or body fluid components, which are undesirable for the contemplated use of the naturally occurring material or composition.

EXAMPLES

The following non-limiting examples have been carried out to illustrate embodiments of the invention.

Example 1: Preparation of eggshell membrane flakes and powder. The following example relates to the preparation of eggshell membrane flakes and powder. Hen eggshells and attached eggshell membrane were obtained from an egg breaking facility. The eggshell membrane was first separated from eggshells and dried to a moisture content of about 10% or less. Eggshell membrane flakes were collected and immediately packaged in plastic bags and placed in storage. Powdering was accomplished using standard milling or pulverizing procedures to treat eggshell membrane flakes containing about 10% moisture. The powder was subsequently sized by screening the pulverized powder through a series of calibrated screens to produce a particle size range from about 100-500 microns.

Example 2: Activation of two types of leukocytes by eggshell membrane. The eggshell membrane (ESM) test product was prepared for addition to in vitro cell cultures in the following manner: 0.5 g dry product was added to 5 mL of phosphate-buffered saline (PBS). This was allowed to sit at room temperature for an hour, centrifuged to precipitate solids, and the supernatant was then sterile-filtered through a 0.22 micron cellulose-acetate syringe filter. This filtrate corresponded to 100 mg/mL ESM stock solution. All subsequent dilutions were also prepared in PBS. Adding a dilution to cell cultures resulted in a further 10-fold dilution.

Freshly purified peripheral blood mononuclear cells (PBMCs) obtained from healthy human volunteers were used for this assay. PBMCs were plated in 96-well microassay plates in triplicate. Negative control wells in triplicate were left untreated. Treatment with human recombinant Interleukin-2 (IL-2) alone, a known immune cell activator, served as a positive control. IL-2 was used at a dilution of 50 international units per mL (IU/mL) and treatment with IL-2 was performed both with and without ESM dilutions. After 18 hours of culture, cells were stained for the activation molecule CD69 on the surface of CD3-negative, CD56-positive natural killer (NK) cells, and on CD3-positive T lymphocytes.

Both leukocyte cell types exhibited moderate CD69 activation with ESM. At 10 mg/mL, ESM produced a 48% increase in cell-surface CD69 expression in NK cells and a 26% increase in CD69 expression in T lymphocytes. When the cells were co-cultured with both ESM (10 mg/mL) and IL-2 (50 IU/mL), CD69 expression was increased by 214% in NK cells and 92% in T lymphocytes. This latter data indicates a co-stimulatory synergy between ESM and IL-2.

Example 3: Treatment of subclinical mastitis in dairy cows. Eggshell membrane (ESM) powder was prepared as described in Example 1. Ten (10) grams of the ESM powder was administered orally to twelve dairy cows twice daily (a total of 20 g of ESM per day). Each cow was initially evaluated for head up/head down, a 5-point mobility index (1=no pain, normal gait; 2=mild pain, unusual gait; 3=moderate pain, some limping; 4=moderate pain, noticeable limping, 5=severe pain, difficulty in moving), milk production (in lbs), and somatic cell count (SCC). At the beginning of the study, 5 (42%) of the cows would enter the barn with their heads down, the group had a mean mobility index of 2.8±1.1, mean milk production of 64.9±23.3 lbs, and mean SCC of 369,500±674,500 cells/mL. One of the cows went dry at about 3 weeks and was removed from the study, however values already measured (mobility index, milk production, SCC) were carried forward for mean calculations for the remainder of the study. After about 6 weeks of supplementation with ESM powder, the eleven (11) remaining cows all (100%) entered the barn head up (indicating generally feeling well), experienced a 36.4% improved mean mobility index (1.8±0.8), had a slightly lower mean milk production (60.3±22.8 lbs), and had a 20.7% lower mean SCC (293,000±448,600 cells/mL). Accordingly, ESM powder improved the dairy cows' overall health (head up, mobility index) and treated underlying subclinical mastitis as evidenced by reduced mean somatic cell count.

Example 4: Method of identifying candidate compound or candidate mixture of compounds in eggshell, eggshell membrane, or a combinations thereof which treats and/or reduces incidence of subclinical mastitis. The term "candidate compound" refers to any compound for which evidence of treating and/or reducing incidence of subclinical mastitis. The term "candidate mixture of compounds" refers to any combination of two and/or more compounds for which evidence of treating and/or reducing incidence of subclinical mastitis.

Examples of compounds include biological molecules and small molecules. Such evidence includes, for example, evidence that the compound or mixture of compounds treats and/or reduces incidence of subclinical mastitis.

A biological molecule is any molecule which contains more than one nucleotide, saccharide, or an amino acid unit, and has a molecular weight greater than about 450. Molecules that contain more than one nucleotide units include nucleic acids, oligonucleotides and polynucleotides. Molecules that contain more than one saccharide unit include disaccharides, trisaccharides, oligosaccharides (more than four saccharides) and polysaccharides. Molecules that contain more than one amino acid units include oligopeptides, peptides, proteins, and polypeptides.

Biological molecules further include derivatives of any of the molecules described above. For example, derivatives of biological molecules include lipid and glycosylation derivatives of molecules that contain more than one amino acid unit, e.g., lipoproteins and glycoproteins. Derivatives of biological molecules further include lipid and glycosylated derivatives of molecules that contain more than one saccharide unit, e.g. lipopolysaccharides and glycopolysaccharides. Derivatives of biological molecules further include proteo-derivatives of molecules that contain more than one nucleotide units.

Small molecules are typically organic compounds, including organometallic and organosilicon compounds, and the like, and generally have molecular weights of approximately 450 or less. Small molecules can further include molecules that would otherwise be considered biological molecules, except their molecular weight is not greater than approximately 450. Thus, small molecules can include monosaccharides, oligosaccharides, amino acids, oligopeptides, nucleotides, oligonucleotides, and their derivatives, having a molecular weight of approximately 450 or less.

A small molecule can have any molecular weight. They are merely called small molecules because they do not qualify as biological molecules, and typically have molecular weights less than approximately 450.

The method for identifying a candidate compound or candidate mixture of compounds includes separating an eggshell membrane from an egg white and eggshell using any suitable mechanical and/or chemical technique known in the art.

The eggshell membrane may be subjected to a solubilization process for solubilizing at least one biological molecule or small molecule from the eggshell membrane. The eggshell membrane may also be subjected to hydrolysis by a suitable means known in the art.

The resulting solubilized or hydrolyzed components can be additional methods to further purify, isolate, and/or concentrate the components. For example, once the proteinaceous material or compounds are solubilized or hydrolyzed, one skilled in the art can use standard biochemistry methods to isolate a protein or compound of interest. Examples of such methods include all types of chromatography (e.g., high pressure liquid chromatography (HPLC) and column chromatography), fractional distillation, and extracting techniques using various solvents. Examples of useful solvents include water, alcohols (e.g., methanol, ethanol, butanol, and propanol), dimethyl sulfoxide, dimethyl formamide, tetrahydrofuran, hexane, ethyl acetate, and chloroform, and/or any mixtures thereof.

The method for identifying a candidate compound or candidate mixture of compounds further includes contacting the compound or mixture of compounds with a gastrointestinal tract cell. The gastrointestinal cell can be any cell type found in the gastrointestinal tract, including, for example, epithelial cells, endothelial cells, smooth muscle cells, endocrine cells, secretory cells, mucosal cells, and absorptive cells of the intestinal epithelium. Gastrointestinal tract cells include, for example, a tonsil cell, esophageal cell, stomach cell, pancreatic cell, pancreatic beta cell, colonic cell, intestinal cell (e.g., small intestinal cell and large intestinal cell), as well as a distal ileum cell. The contacting may be performed via in vitro or in vivo methods.

In vitro methods typically include mixing the compound or mixture of compounds with suitable cells in a culture medium. The order of adding the compound or mixture of compounds and the cells to the culture medium is not critical. The gastrointestinal tract cells may be independent of other cells, or may be associated with other cells.

In vivo methods typically involve the administration of the compound or mixture of compounds, such as those described above, to the gastrointestinal cell of a mammal, preferably a human or laboratory mammal. The compounds or mixture of compounds useful in the methods of the present invention are administered to a mammal in an amount that, for example, decreases somatic cell counts in milk. The administered amount may vary over a large range, and may be determined during pre-assay tests by methods familiar to one of ordinary skill in the art.

The compound or mixture of compounds useful in the methods of the present invention may be administered to a ruminant by any of a number of well-known methods for administering compounds or mixture of compounds. For example, the compound or mixture of compounds may be administered orally (including to laboratory animals by gavage), sublingually, intravenously, intranasally, intramuscularly, subcutaneously, or transdermally. Other routes of administration include intubation, which refers to placement of a nasogastric feeding tube or a gastric feeding tube into the body of a laboratory animal.

After the compound or mixture of compounds has had time, for example, to decrease somatic cell counts, the method further includes obtaining a biological sample from the mammal, and determining the candidate compound or a candidate mixture of compounds that treats and/or reduces incidence of subclinical mastitis.

What is claimed is:

1. A method for treating subclinical mastitis, said method comprising orally administering to a ruminant in need thereof an effective amount of a composition comprising a naturally occurring material derived from eggshell membrane, wherein the effective amount achieves at least about a 0.5 percentage decrease in somatic cell count thereby treating, reducing or preventing the subclinical mastitis.

2. The method of claim 1, wherein the effective amount is effective to achieve at least about a 1 percentage point decrease in somatic cell count.

3. The method of claim 1, wherein the effective amount is effective to achieve at least about a 2 percentage point decrease in somatic cell count.

4. The method of claim 1, wherein the effective amount is effective to achieve at least about a 5 percentage point decrease in somatic cell count.

5. The method of claim 1, wherein the naturally occurring material is selected from the group consisting of a hexosamine, a glycosaminoglycan, hyaluronic acid, sialic acid, a collagen, elastin, other egg proteins or glycoproteins, lysozyme, ovotransferrin, lysyl oxidase, and/or a combination thereof.

6. The method of claim 5, wherein the hexosamine is glucosamine and/or N-acetylglucosamine.

7. The method of claim 5, wherein the glycosaminoglycan is chondroitin sulfate, dermatan sulfate, keratan sulfate, heparan sulfate, and/or a combination thereof.

8. The method of claim 1, wherein the naturally occurring material is water soluble.

9. The method of claim 1, wherein the naturally occurring material is water insoluble.

10. The method of claim 1, wherein the naturally occurring material comprises the following in weight percent:

a) about 0.1 to about 5 wt % hexosamine;

b) about 0.1 to about 3 wt % glycosaminoglycan;

c) about 0.5 to about 5 wt % hyaluronic acid;

d) about 0.01 to about 2 wt % sialic acid; and/or e) about 3 to about 20 wt % collagen.

11. The method of claim 1, wherein the naturally occurring material is an eggshell membrane powder.

12. The method of claim 1, wherein the naturally occurring material is an eggshell membrane extract.

13. The method of claim 1, wherein the naturally occurring material is an eggshell membrane hydrolysate.

14. The method of claim 1, wherein the naturally occurring material is an eggshell membrane isolate.

15. The method according to claim 1, wherein the eggshell membrane is a fowl eggshell membrane.

16. The method according to claim 1 further comprising, orally administering to the ruminant, about 10 g-20 g of the composition daily.

* * * * *